United States Patent
Murtagh

(10) Patent No.: US 7,409,881 B2
(45) Date of Patent: Aug. 12, 2008

(54) BOUND MATERIALS CORE MEASURING DEVICE

(76) Inventor: Brian James Murtagh, 4 Holme Close, Hatfield Garden Village (GB) AL10 9LQ (*) Notice: Subject to any disclaimer, the term of this patent is extended or adjusted under 35 U.S.C. 154(b) by 245 days.

(21) Appl. No.: 10/576,590

(22) PCT Filed: Oct. 28, 2004

(86) PCT No.: PCT/GB2004/004571
§ 371 (c)(1), (2), (4) Date: May 24, 2006

(87) PCT Pub. No.: WO2005/045423
PCT Pub. Date: May 19, 2005

(65) Prior Publication Data
US 2007/0084301 A1    Apr. 19, 2007

(30) Foreign Application Priority Data
Oct. 30, 2003   (GB) ................... 0325338.2

(51) Int. Cl.
*B01L 3/00* (2006.01)
(52) U.S. Cl. .................................. 73/864.91
(58) Field of Classification Search .............. 73/864.45, 73/864, 864.91; 33/834
See application file for complete search history.

(56) References Cited

U.S. PATENT DOCUMENTS

| | | | | |
|---|---|---|---|---|
| 3,935,834 A | * | 2/1976 | Buhrmann, Jr. | 116/216 |
| 5,382,120 A | | 1/1995 | Parsons | 408/16 |
| 6,298,574 B1 | | 10/2001 | Baker | 33/834 |

FOREIGN PATENT DOCUMENTS

GB    2326722 A   * 12/1998

* cited by examiner

*Primary Examiner*—Hezron E. Williams
*Assistant Examiner*—Tamiko D Bellamy
(74) *Attorney, Agent, or Firm*—Edwin D. Schindler

(57) ABSTRACT

A bound materials core measuring device includes a tubular body to accommodate a core sample of road or pathway surfacing bound material. The tubular body has a plurality of graduated scales extending therealong at spaced intervals therearound to enable the core sample to be measured from a plurality of angles by reading from each of the plurality of graduated scales. The tubular body has, located therein, a supporting element for supporting the core sample with the supporting element being mounted for longitudinal movement relative to the tubular body. The tubular body also includes therein a device for effecting the longitudinal movement.

9 Claims, 1 Drawing Sheet

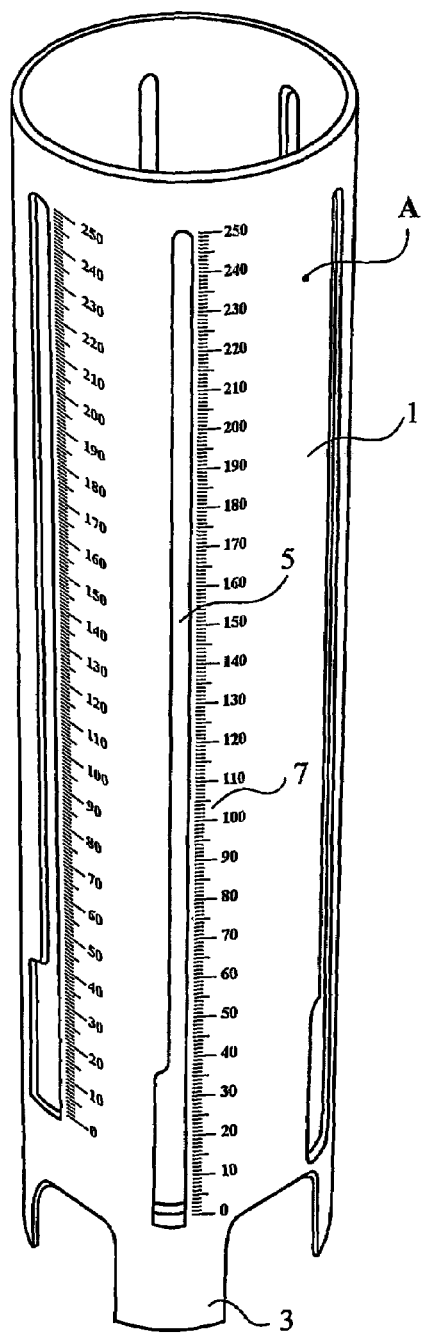
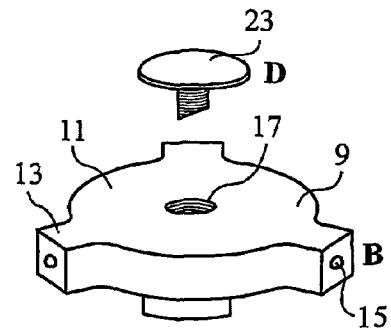
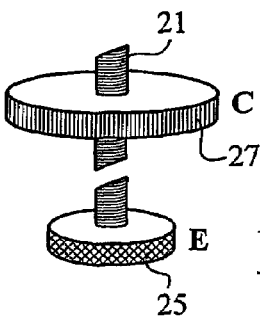
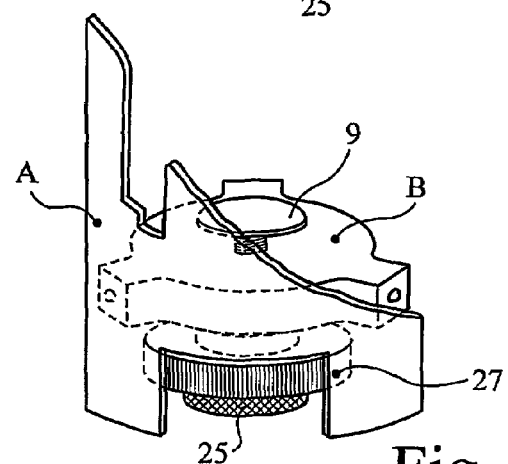
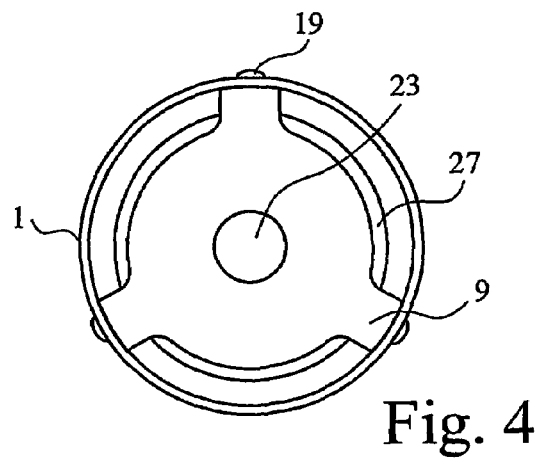
Fig. 1
Fig. 3
Fig. 2
Fig. 4

US 7,409,881 B2

BOUND MATERIALS CORE MEASURING DEVICE

FIELD OF THE INVENTION

The present invention relates to devices for the core measuring of bound materials, such devices being suitable, for example, for measuring the thickness of layers of surfacing material of a surfaced road or footway. Such bound material may be, for instance, cement-bound or bitumen-bound.

BACKGROUND TO THE INVENTION

The quality and depth of road and footway surfacing plays an important role in safety for the road and pathway users. Partial subsidence or rucking of the surfacing material may trip a pedestrian on a footway or deflect the tyres of a road vehicle risking loss of control by the motorist.

Highways legislation covering the mandatory requirements for road and pavement quality and particularly depth of surfacing layers has tightened up considerably over recent years. Under the New Roads and Street Works Act, 1991 the allowed tolerance for thickness of upper surfacing layer or "wearing course" is to be within +10 mm to −5 mm of a specified thickness for a given material—most commonly 40 mm. Very substantial penalties are exacted for failure to meet this requirement.

Through safety consciousness and the impact of the stringent legal obligations, those whose work entails excavating roads and pathways are obliged to take great care when reinstating those roads or pathways and are subject to official inspection of their reinstatement work. In the case, for example, of cable television engineers who routinely channel through hundreds of miles of roads and footways to provide cable access to millions of consumers there is a very major budgetary burden to ensure that the roads and footways are properly reinstated and failure to meet the statutory requirement for surfacing layer thickness on inspection can greatly increase their operating costs. Accordingly, it is very important to them to have a demonstrably precise and reliable gauge for measuring the thickness of core samples taken for inspection.

Conventionally, the core samples for inspection are extracted from the site as vertical cylinders of the bound material generally between 100 mm and 150 mm in diameter and up to 300 mm in depth although generally the most important portion to be measured, the wearing course, constitutes only the first 40 mm or so. The core samples are sent to a government laboratory for measurement, taking days and weeks to process and removing any opportunity for witnessing or validation of the results. GB-A-2326722 discloses a bound materials core measuring device comprising a free-standing, rigid, transparent or apertured tubular body adapted to accommodate a core sample of road or pathway surfacing bound material and having a plurality of graduated scales extending therealong at spaced intervals therearound so as to enable the sample to be viewed through the body and the depth of the relevant one or more layers of the core sample to be measured from a plurality of angles by reading from each of the plurality of graduated scales.

The device disclosed in GB-A-2326722 has a plurality of fins extending across the tubular body which support any core sample held within the tubular body. The use of fin supports enable debris to drop away from beneath the core sample resting at the bottom of the tubular body to eliminate associated measurement errors. The fins serve also as support legs for the tubular body which extend from within the tubular body to the exterior thereof.

The baseline zero of the graduated scales is at the level on the tubular body at which a core sample comes to rest when placed in the tubular body. The fin legs are suitably adjustable to ensure that they are level with the baseline zero level before measuring commences.

STATEMENTS OF THE INVENTION

According to the present invention there is provided a bound materials core measuring device which comprises a tubular body adapted to accommodate a core sample of road or pathway surfacing bound material and having a plurality of graduated scales extending therealong at spaced intervals therearound so as to enable the sample to be viewed through the body and the depth of the relevant one or more layers of core sample to be measured from a plurality of angles by reading from each of the plurality of graduated scales, wherein the tubular body has, located therewithin, means for supporting said core sample, said means being mounted for longitudinal movement relative to said tubular body and means, located within said tubular body, for effecting said longitudinal movement.

Preferably said tubular body comprises a rigid, transparent or apertured body.

Preferably said means for supporting said core sample includes a base member attached to the tubular body and, extending upwardly from said base member, a core support element. More preferably said core support element is mounted for longitudinal movement relative to said base member. Most preferably said core support element extends through said base member and includes an adjustment member located below said base member. The core support element may be screw threadingly engaged with said support member.

BRIEF DESCRIPTION OF THE DRAWINGS

The accompanying drawings are as follows:

FIG. 1 is a perspective view of a bound materials core measuring device in accordance with the present invention FIG. 2 shows in more detail the lower part of the device of FIG. 1;

FIG. 3 is an exploded perspective view of the core support means of the device of FIG. 1; and FIG. 4 is a top plan view of the device of FIG. 1.

DETAILED DESCRIPTION OF THE INVENTION

An embodiment of the invention will now be described, by way of example only, with reference to the accompanying drawings.

Referring to FIG. 1 of the accompanying drawings, a bound materials core measuring device comprises a circular cylindrical tubular body 1 of stainless steel or other relatively robust material capable of withstanding the highly abrasive nature of bound material core samples. Tubular body 1 is open-ended at both top and bottom and is provided with three integral, equally peripherally spaced apart legs 3, there being a considerable gap between each pair of adjacent legs, as illustrated in FIG. 1.

Although the metal tubular body 1 is opaque, the layers of the core sample may be viewed through each of six longitudinal apertures 5 spaced at equal intervals around the tubular body 1. Each of these apertures, or viewing ports, 5 has a scale 7, graduated in mm, running alongside it from a zero baseline located just above the level of the legs 3. For the first 80 mm or so of its length, which corresponds to the wearing course of the core structure, each aperture 5 is relatively wide, suitably of the order of 6 mm. Above this height, the aperture, which extends for approximately 250 mm in the illustrated example, is of approximately half this breadth. This is because viewing is less crucial above the first 80 mm and reducing the breadth of the aperture allows the strength of the tubular body 1 to be optimised.

The material of the tubular body 1 is chamfered along the aperture, adjacent scale 7, to provide reduction in any "parallax error" (due to the wall thickness of the cylinder affecting the accurate reading of the measurement). The chamfering of the body wall brings, in effect, the scale closer to the sample.

Located at the bottom of the cylinder, below the graduated scales, is a circular support member in the form of a boss 9 which has a substantially circular central portion 11 and, extending therefrom, three radially outwardly extending, equally spaced apart peripherally, arms 13. Each arm 13 is provided with a threaded blind bore 15. In the centre of the central portion 11 there is located a threaded through bore 17 extending from the upper to the lower surface of the boss 9.

The central circular portion 11 has a diameter which is about 50% of that of the cylinder 1. The three radial arms 13 have a width about one sixth of the circumference of cylinder 1, the length of each arm is such that the distance from the outer surface of each arm to the centre of circular portion 11 is close to that of the internal radius of cylinder 1 so that the boss fits snugly within cylinder 1 and can be connected thereto by means of screws 19 extending through the body of cylinder 1 into the blind threaded bores 15.

Extending through boss 9, and in threaded engagement therewith within through bore 17, is a threaded rod 21 having an integral fixed domed head 23 at its upper end. At its lower end rod 21 is provided with a knurled disc 25 which is also rigidly attached to rod 21. Located between disc 25 and the under surface of boss 9 is a threaded knurled disc 27 which is of greater diameter than disc 25 and which has a central threaded hole by which disc 27 is in screw threaded engagement with rod 21.

The threaded rod 21 carrying domed head 23 may be rotated by means of disc 25, accessed through the spaces between legs 3. Such rotation will cause the height of domed head 23 to be varied longitudinally with respect to cylinder 1. With a sample in position, therefore movement of head 23 may be effected to adjust the bottom of the sample to the height of the zero of the scales 7. The further disc 27 may then be turned so that it moves into engagement with the lower surface of boss 9 to lock the threaded rod in position.

In this way the overall device is very compact and yet it is very simple to adjust the bottom of the sample to the zero of the scales by a simple turning movement applied to the threaded rod 21 carrying the domed head 23.

The invention claimed is:

1. A bound materials core measuring device, comprising:
    a tubular body for accommodating a core sample of road or pathway surfacing bound material, said tubular body including a plurality of graduated scales extending therealong at spaced intervals therearound for enabling the core sample to be viewable through said tubular body with depth of one or more layers of the core sample being measured from a plurality of angles by reading each of said plurality of graduated scales;
    means for supporting the core sample within said tubular body, said means for supporting being mounted for longitudinal movement relative to said tubular body; and,
    means for effecting said longitudinal movement located within said tubular body.

2. The bound materials core measuring device according to claim 1, wherein said tubular body is a rigid body.

3. The bound materials core measuring device according to claim 1, wherein said tubular body is a transparent body.

4. The bound materials core measuring device according to claim 1, wherein said tubular body is an apertured body.

5. The bound materials core measuring device according to claim 1, wherein said means for supporting the core sample within said tubular body includes a base member attached to said tubular body and, extending upwardly from said base member, a core support element.

6. The bound materials core measuring device according to claim 5, wherein said core support element is mounted for longitudinal movement relative to said base member.

7. The bound materials core measuring device according to claim 6, wherein said core support element extends through said base member and includes an adjustment member located below said base member.

8. The bound materials core measuring device according to claim 5, wherein said core support element extends through said base member and includes an adjustment member located below said base member.

9. The bound materials core measuring device according to claim 5, wherein said core support member is screw threadedly engaged with said means for supporting the core sample within said tubular body.

\* \* \* \* \*